(12) United States Patent
Gibson

(10) Patent No.: US 8,160,714 B2
(45) Date of Patent: Apr. 17, 2012

(54) COMPLEMENTARY DRUG DELIVERY SHEATH FOR AN IMPLANTABLE MEDICAL DEVICE

(75) Inventor: Peter Gibson, South Coogee (AU)

(73) Assignee: Cochlear Limited, Macquarie University, NSW (AU)

( * ) Notice: Subject to any disclaimer, the term of this patent is extended or adjusted under 35 U.S.C. 154(b) by 953 days.

(21) Appl. No.: 12/168,468

(22) Filed: Jul. 7, 2008

(65) Prior Publication Data

US 2009/0012594 A1      Jan. 8, 2009

Related U.S. Application Data

(60) Provisional application No. 60/948,411, filed on Jul. 6, 2007.

(51) Int. Cl.
*A61N 1/05* (2006.01)
(52) U.S. Cl. ............... 607/55; 607/120; 607/152; 607/3
(58) Field of Classification Search ....................... 607/36
See application file for complete search history.

(56) References Cited

U.S. PATENT DOCUMENTS

| | | | |
|---|---|---|---|
| 6,421,569 B1 | 7/2002 | Treaba et al. | |
| 6,968,234 B2 * | 11/2005 | Stokes | 607/36 |
| 2005/0196421 A1 | 9/2005 | Hunter et al. | |
| 2008/0161871 A1 * | 7/2008 | Knapp et al. | 607/5 |

OTHER PUBLICATIONS

International Search Report mailed Sep. 19, 2008 corresponding PCT/US08/069332; filed Jul. 7, 2008, published as WO/2009/009487 on Jan. 15, 2009; Applicant Cochlear Americas; Inventors: Peter Gibson.
"International Preliminary Report on Patentability" mailed Aug. 14, 2009 corresponding PCT/US2008/69332, filed Jul. 7, 2008, published as WO/2009/009487 on Jan. 15, 2009; Applicant Cochlear Americas; Inventors: Peter Gibson.
Written Opinion dated Sep. 19, 2008; corresponding PCT/US08/069332 filed Jul. 7, 2008 published as WO/2009/009487 on Jan. 15, 2009; Applicant: Cochlear Americas; Inventors: Peter Gibson.

* cited by examiner

*Primary Examiner* — Carl H Layno
*Assistant Examiner* — Natasha Patel
(74) *Attorney, Agent, or Firm* — Kilpatrick, Townsend & Stockton, LLP.

(57) ABSTRACT

A complementary drug delivery sheath for implantable medical devices. The complementary drug delivery sheath is covered, impregnated or otherwise carries one or more drugs. The complementary drug-delivery sheaths are manufactured separately from to the implantable device and are operationally combined with the device subsequent to the device's manufacture and/or sterilization. For example, embodiments of the complementary drug-delivery sheaths may be configured, for example, to attain an implanted position adjacent to one or more surfaces of an implantable medical device. In certain embodiments, the sheath is configured in the form of a glove, pocket, pouch, or the like to receive and to partially or completely wrap around or envelop an implantable medical device. Embodiments of the complementary drug delivery sheath may be implanted into the recipient prior to, concurrently with, or subsequent to the implantation of the implantable medical device.

35 Claims, 6 Drawing Sheets

US 8,160,714 B2

COMPLEMENTARY DRUG DELIVERY SHEATH FOR AN IMPLANTABLE MEDICAL DEVICE

CROSS-REFERENCE TO RELATED APPLICATIONS

This application claims the benefit of U.S. Provisional Patent Application 60/948,411, filed on Jul. 6, 2007, which is hereby incorporated by reference herein

BACKGROUND

1. Field of the Invention

The present invention relates generally to implantable medical devices, and more particularly, to a complementary drug delivery sheath for an implantable medical device.

2. Related Art

Implantable medical devices are capable of providing a wide range of benefits to a patient. For example, implantable prosthetic hearing devices process ambient sound to supplement or provide hearing ability to hearing impaired patients (sometimes referred to herein as "recipients").

Implantable prosthetic hearing devices include a category of implantable devices known as Cochlear™ implants (also referred to as Cochlear™ devices, Cochlear™ implant devices, and the like; "cochlear implants" herein). (COCHLEAR is a trademark of Cochlear Limited, Lane Cove, NSW, Australia.) In cochlear implants, an array of stimulation electrodes is implanted in a recipient's cochlea. This array is controlled by an electronic system encased in a hermetically sealed, biocompatible housing typically implanted in the mastoid. The electronic system essentially contains decoder and driver circuits for the stimulation electrodes. Acoustic sound reception and conversion of acoustic signals into electrical signals typically occurs externally in a sound processor worn by the recipient. The sound processor superimposes the preprocessed signals, properly coded, on a high frequency carrier signal which is transmitted transcutaneously to the implanted components through the closed skin. A microphone is located outside of the recipient's body, typically in a behind-the-ear housing worn on the auricle.

Traditionally, there has been interest in delivering bioactive substances or chemicals (generally and collectively referred to herein as "drugs") in conjunction with a cochlear implant and other implantable medical devices for a variety of purposes. For example, in one conventional approach the implantable medical device is coated with a bioactive substance. In another conventional approach a bioactive substance is integrated into the polymeric coating of the implantable medical device. In other conventional approaches various techniques for delivering drugs in liquid form to a target location in a patient from an external or implanted reservoir.

These and other conventional approaches typically require the incorporation of the drug into the implantable medical device during the manufacturing process of the device. This introduces a number of difficult problems and challenges for the manufacturing and sterilization processes, particularly for complex implantable medical devices. On the other hand, the use of reservoirs provides significant limitations to many aspects of the administration of the drug therapy.

SUMMARY

In accordance with one aspect of the present invention, a kit of implantable components for implantation in a recipient is disclosed. Embodiments of the kit comprise an implantable medical device and a drug delivery sheath physically separate from the device and configured to be implanted in the recipient proximate to the device, comprising: at least one pannicular substrate configured to be operably positioned adjacent to one or more surfaces of the device subsequent to the device's manufacture, and at least one drug carried on the at least one substrate so as to be released into the recipient.

In accordance with a second aspect of the present invention, a complementary drug-delivery sheath for implantation into a recipient of an implantable medical device is disclosed. Embodiments of the complementary drug-delivery sheath comprise: a pannicular substrate having dimensions which enable the sheath to be implanted proximate to one or more surfaces of the device; and at least one drug carried in the substrate for release into the body of the recipient.

BRIEF DESCRIPTION OF THE DRAWINGS

Illustrative embodiments of the present invention are described herein with reference to the accompanying drawings, in which.

DETAILED DESCRIPTION

The present invention is generally directed to a complementary drug-delivery sheath for implantable medical devices. Embodiments of the complementary drug-delivery sheath are covered, impregnated or otherwise carry one or more drugs and, as such, are at times referred to herein as drug-delivery sheaths.

Embodiments of the complementary drug-delivery sheaths physically separate from the implantable medical device and, as such, may be manufactured separately from to the implantable medical device. The complementary drug-delivery sheath is operationally combined with the implantable medical device subsequent to the device's manufacture and/or sterilization. For example, embodiments of the complementary drug-delivery sheath may be configured, for example, to attain an implanted position adjacent to one or more surfaces of an implantable medical device. In certain embodiments, the sheath is configured in the form of a glove, pocket, pouch, or the like (collectively and generally referred to as a "pouch" herein), to receive and to partially or completely wrap around or envelop ("envelop" herein) all or a portion of an implantable medical device. Embodiments of the complementary drug delivery sheath may be implanted into the recipient prior to, concurrently with, or subsequent to the implantation of the implantable medical device.

Providing an independently-manufactured and physically distinct, complementary drug delivery sheath to an implantable medical device increases flexibility in the applied therapy while reducing the undesirable aspects associated with manufacturing an implantable medical device with a drug integrated therein. For example, this enables manufacturing efforts to be focused solely on the successful manufacture of the implantable medical device rather than on manufacturing an integrated assembly of the device and drug-delivery mechanism. Additionally, the implantable medical device may be manufactured as a universal device which may be complemented with different embodiments of the drug-delivery sheath. This advantageously enables a single implantable component to be manufactured and inventoried for a length of time not determined by a drug. This is particularly advantageous in those circumstances in which the drug to be delivered via the sheath has a limited shelf life.

As used herein, the term "drug" refers to any bioactive substance now or later developed, including, but not limited to, pharmaceuticals and other chemical compounds such as those intended to provide therapeutic benefits to, or other reactions in, an implant recipient, whether localized or distributed throughout the recipient. Such bioactive substances may include, for example, steroids or other anti-inflammatory drug to reduce inflammation at the implantation site. Another class of bioactive substances that may be included in the drug-delivery sheath are antibiotics to mitigate bacterial growth related to the implantation of the medical device.

Figure 1A:
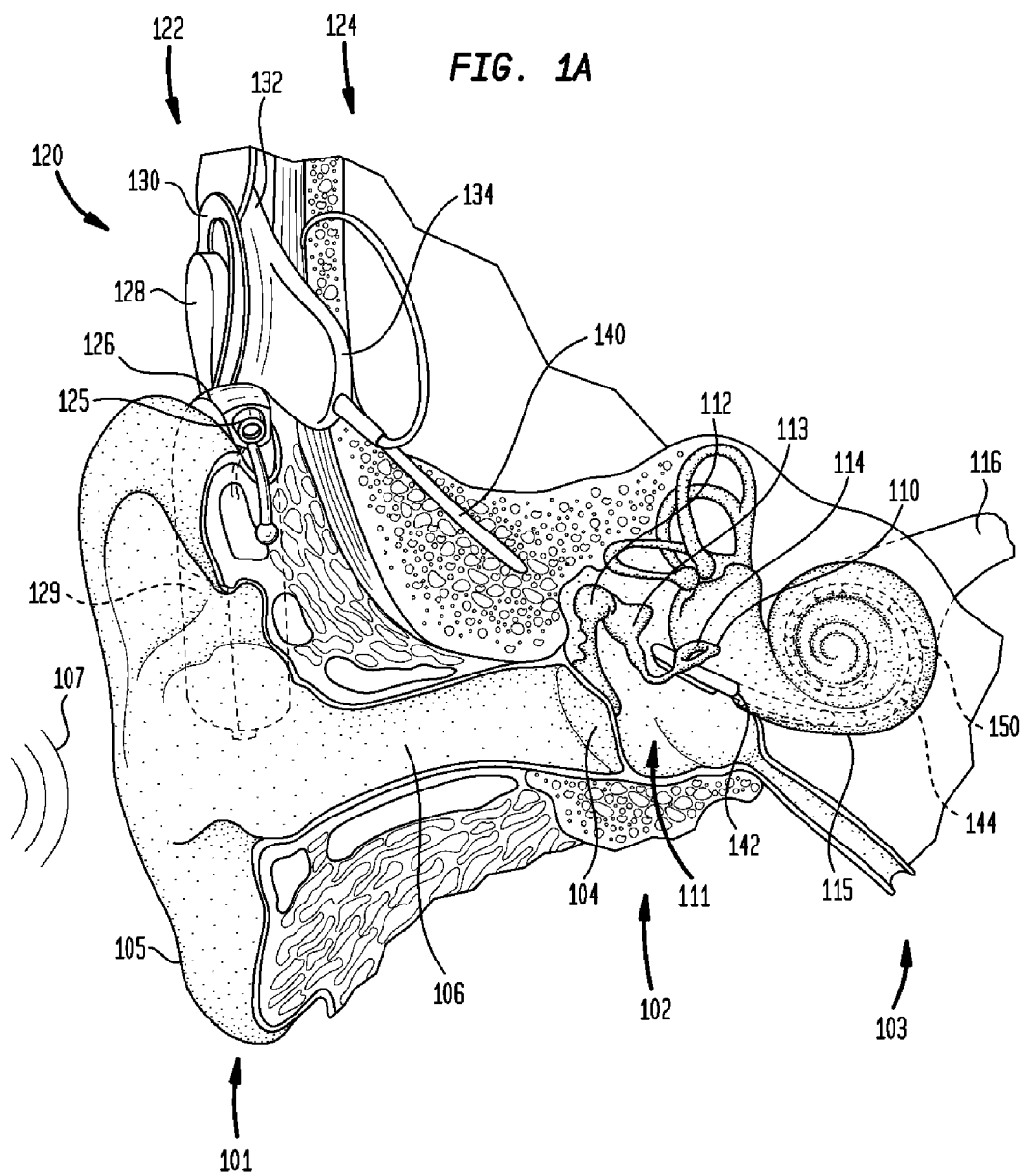
FIG. 1A is an embodiment of a cochlear implant device which may be advantageously complemented with an embodiment of a drug-delivery sheath of the present invention.

FIG. 1A is a perspective view of an exemplary cochlear implant with which a complementary drug-delivery sheath of the present invention may be implemented. In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In deaf persons, there is an absence or destruction of the hair cells. A cochlear implant 120 is utilized to directly stimulate the ganglion cells to provide a hearing sensation to the recipient.

FIG. 1A also shows the positioning of cochlear implant 120 relative to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is outputted to a behind-the-ear (BTE) speech processing unit 126 that generates coded signals which are provided to an external transmitter unit 128, along with power from a power source 129 such as a battery. External transmitter unit 128 comprises an external coil 130 and, preferably, a magnet (not shown) secured directly or indirectly in external coil 130.

Internal component assembly 124 comprise an internal coil housing 132 that receives and transmits power and coded signals received from external assembly 122 to a stimulator unit 134 to apply the coded signal to cochlea 115 via an implanted electrode assembly 140. Electrode assembly 140 enters cochlea 115 at cochleostomy region 142 and has one or more electrodes 150 positioned on an electrode array 144 to be substantially aligned with portions of tonotopically-mapped cochlea 115. Signals generated by stimulator unit 134 are typically applied by an array 144 of electrodes 150 to cochlea 115, thereby stimulating auditory nerve 116.

Given the coiling shape of cochlea 115, cochlear implant devices such as electrode assembly 140 are often constructed using a material, or combination of materials, which curls or is capable of being curled in a manner which follows the curvature of cochlea 115. The portion of electrode assembly 140 intended to be inserted into cochlea 115 will often have a stiffening stylet (not shown) inserted into a channel, for example a lumen (not shown), which extends distally from the proximate end of electrode assembly 140. During implantation of electrode assembly 140, the stylet contained in the lumen of electrode assembly 140 is removed from the proximate end of electrode assembly 140 as electrode assembly 140 is inserted into cochlea 115. The act of removing the stiffening stylet from the lumen allows electrode assembly 140 to curl. In further embodiments of cochlear implant 120, the stiffness of the stylet decreases in response to fluids and/or body temperature allowing electrode assembly 140 to curl in order to follow the curvature of the inner walls of cochlea 115. In other embodiments of cochlear devices, electrode assembly 140 is naturally straight without the assistance of a stylet inserted into the lumen. Electrode assembly 140 is constructed using a flexible material, or is constructed so as to flex upon a fixed amount of force being exerted on the tip or body of electrode assembly 140 as it is being inserted into cochlea 115. In other embodiments, electrode assembly 140 has a length which results in it extending to the first turn of cochlea 115. In further embodiments of implanted cochlear devices, the stylet becomes flexible in response to fluids and/or body temperature thereby allowing electrode assembly 140 to curl so as to follow the curvature of the inner wall of cochlea 115.

As one of ordinary skill in the art will appreciate from the present disclosure, embodiments of the present invention may be advantageously implemented in a variety of implantable medical devices, components, etc. ("devices" herein). Although cochlear implant 120 described above with reference to FIG. 1A is a partially-implantable device, embodiments of the present invention provide particular benefits to devices which have limited sources of power such as fully-implantable prosthetic hearing devices including fully-implantable bone-anchored hearing aids, fully-implantable cochlear implants, middle ear implants, and the like.

Figure 1B:
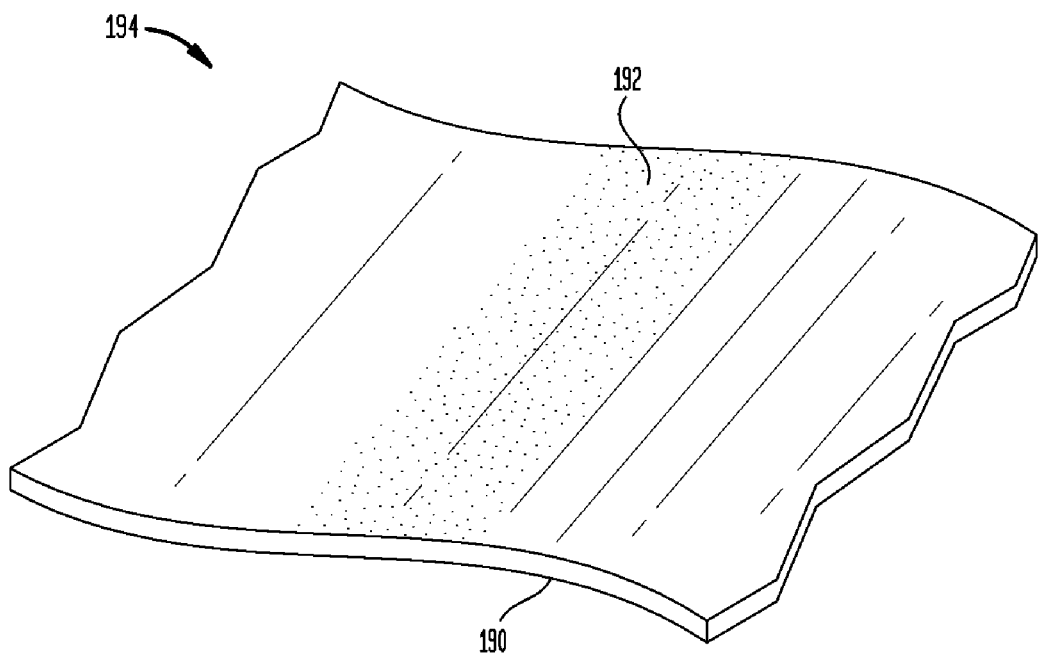
FIG. 1B is a perspective view of a region or portion of a drug-delivery sheet of the present invention showing a pannicular substrate on which components of a drug are releasably secured, in accordance with embodiments of the present invention.

FIG. 1B is a perspective view of a region or portion of an exemplary drug-delivery sheath 194 of the present invention.

Drug-delivery sheath 194 comprises a pannicular substrate 190. A drug 192 is carried in or on (collectively and generally "in" herein) substrate 190; that is, a drug 192 is releasably secured in substrate 190 such that drug 192 is implanted in the recipient with sheath 194, and is subsequently released in to the body of the recipient in which the drug-delivery sheath 194 and its complimentary implantable medical device (not shown in FIG. 1B) are implanted. For ease of illustration, components of drug 192 are schematically illustrated as small solid circles distributed across a distinct region of substrate 190. It should be appreciated, however, that the quantity of different drugs, the amount of each such drug, the location of such drug or drugs, and so on, may be determined based on the particular substrate 190, drug or drugs 192, the condition or conditions to be treated by the drug or drugs, the implant location, recipient physiology and other factors.

Substrate 190 may be composed of a variety of materials, and have a variety of structures, depending on the particular application and type of drug(s) 192 which substrate 190 is to carry. Embodiments of substrate 190 are described below. It should also be appreciated that the mechanism by which drug 192 is releasably secured to substrate 190 may be a characteristic of substrate 190, a characteristic of drug 192, or a characteristic of both substrate 190 and drug 192. Additionally or alternatively, an additional treatment or agent may be employed to releasably secure drug 192 to substrate 190.

Figure 2A:
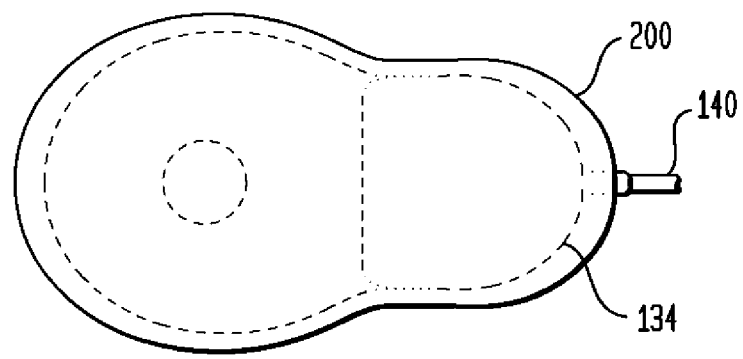
FIG. 2A is a top view of an embodiment the present invention comprising a single drug-delivery sheath configured to be disposed on top of an implantable medical device such as the stimulator unit illustrated in FIG. 1A when the stimulator unit is implanted in a recipient.
Figure 2B:
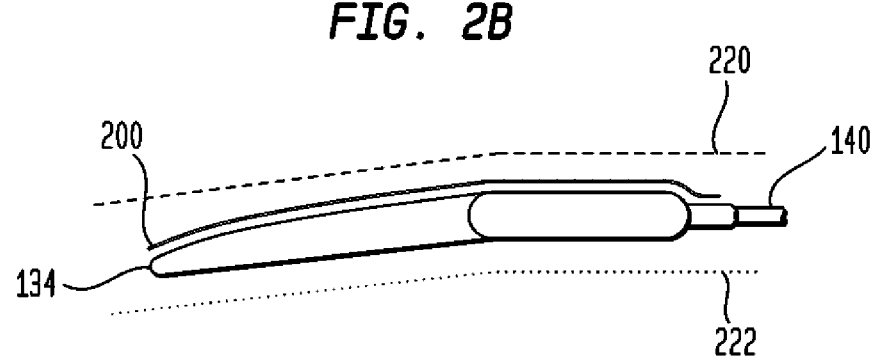
FIG. 2B is a side view of the embodiment the present invention illustrated in FIG. 2A.

FIGS. 2A and 2B are top and side perspective views, respectively, of one embodiment of a complementary drug-delivery sheath of the present invention, referred to herein as complementary drug-delivery sheath 200. This illustrative embodiment of complementary drug-delivery sheath 200 is configured to be positioned adjacent to and above stimulator unit 134 of cochlear implant 120 (FIG. 1) when stimulator unit 134 is implanted in a recipient. This is shown schematically in FIG. 2B. FIG. 2A is a top view of such an arrangement of stimulator unit 134 and drug-delivery sheath 200; FIG. 2B is a side view of stimulator unit 134 and drug-delivery sheath 200 shown in an implanted position; that is, disposed between a recipient's skin 220 and a recessed portion of mastoid bone 222.

Figure 3A:
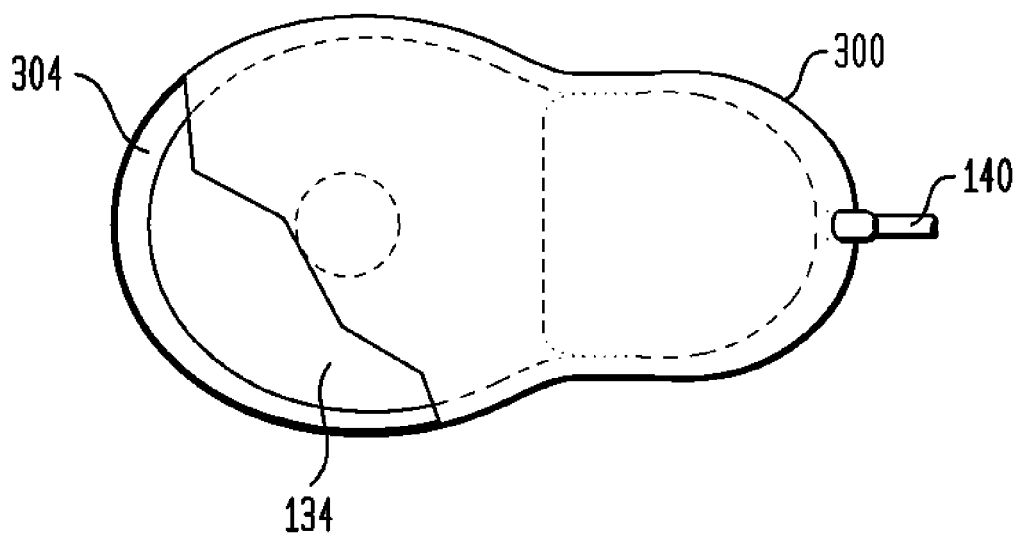
FIG. 3A is a side view of an embodiment the drug-delivery sheath of the present invention in the form of a conformal pouch or pocket configured to receive an implantable medical device such as the stimulator unit illustrated in FIG. 1A.
Figure 3B:
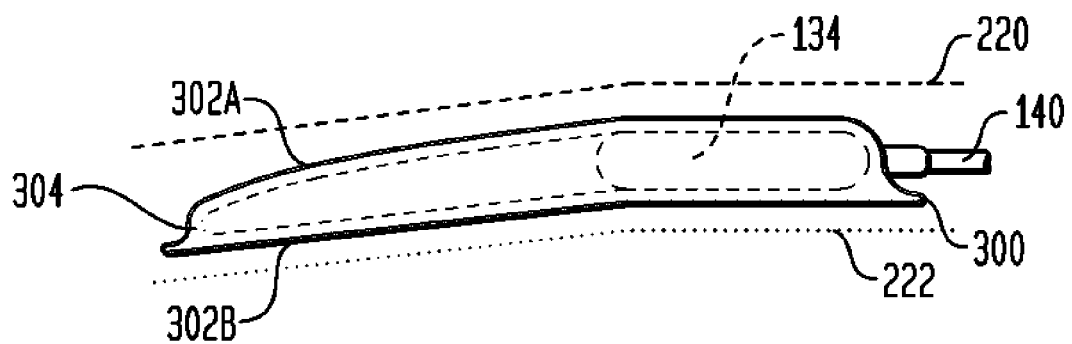
FIG. 3B is a side view of the embodiment the present invention illustrated in FIG. 3A.

FIGS. 3A and 3B are top and side perspective views, respectively, of another embodiment of a complementary drug-delivery sheath of the present invention, referred to herein as complementary drug-delivery sheath 300. This illustrative embodiment of the complementary drug-delivery sheath is configured as a pouch that partially or substantially wraps around or envelops stimulator unit 134 (FIG. 1). As shown in FIG. 3A, drug-delivery sheath 300 comprises a top sheath 302A and a bottom sheath 302B that are permanently or temporarily joined together to form a pouch 304 configured to receive stimulator unit 134. As such, sheath 300 wraps around and substantially conforms to the surface of stimulator unit 134. It should be appreciated that in alternative embodiments, top sheath 302A and a bottom sheath 302B are manufactured as a single, unitary drug-delivery sheath.

Figure 4:
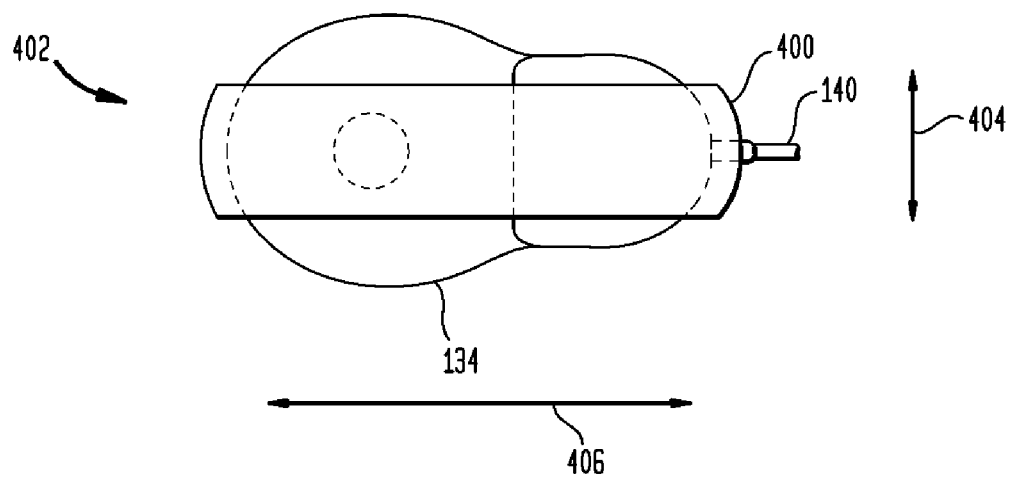
FIG. 4 is a top view of an embodiment the present invention having a drug-loaded component sheath configured to be partially disposed on the stimulator unit illustrated in FIG. 1A.

In the embodiments of the drug-delivery sheath described above, the sheath is generally shaped to have one or more exterior dimensions that approximate the corresponding exterior dimensions of the implantable medical device it complements, here, stimulator unit 134. It should be understood, however, that the shape and size of other embodiments of the drug-delivery sheath may vary depending on the particular application. For example, FIG. 4 is a top view of a drug-delivery sheath 400 configured to be positioned proximate to a central region 402 of stimulator unit 134. In this exemplary embodiment, in lateral direction 404 drug-delivery sheath 400 has a perimeter that is encompassed within the corresponding perimeter of stimulator unit 143 that it complements. In longitudinal direction 406 drug-delivery sheath 400 has a perimeter that approximates the corresponding perimeter of stimulator unit 134.

Such embodiments may be useful in those applications in which it is desirable to minimize the size of the drug-delivery sheath being implanted in the recipient, for example, to limit the amount of drugs delivered to the recipient, or due to the location or dimension of the implant site.

Figure 5:
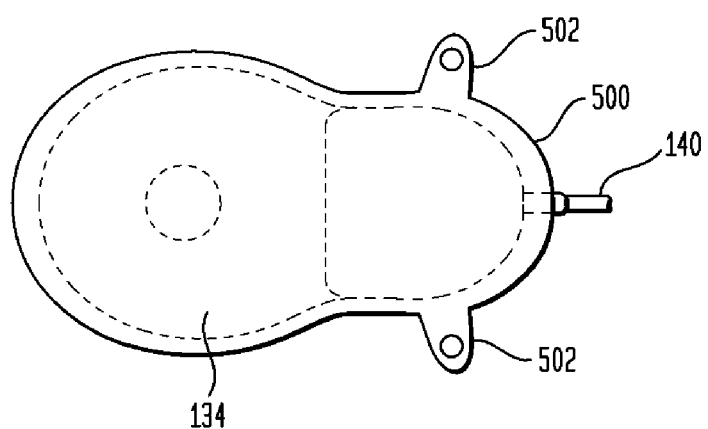
FIG. 5 is a top view of an alternative embodiment a drug-delivery sheath configured to be secured at the implant site for the implantable medical device.

FIG. 5 is a top view of an alternative embodiment of a drug-delivery sheath of the present invention. Drug-delivery sheath 500 comprises additional securing tabs or flaps 502. Securing flaps 502 are configured to attach drug-delivery sheath 500 to the implantable medical device, or other component or anatomical structure. In this illustrative embodiment, securing tabs 502 are provided to enable drug-delivery sheath 500 to be secured directly to neighboring tissue 220 (FIG. 2) and/or mastoid bone 222 (FIG. 2). As such, securing tabs 502 prevent drug-delivery sheath 500 from migrating from the implantation site. Securing tabs 502 may be attached to the desired object using an appropriate method such as sutures, staples, adhesives, or other attaching methods and techniques now or later developed.

As one of ordinary skill in the art should appreciate, other securing mechanisms may be integrated into embodiments of drug-delivery sheath of the present invention other than tabs 502. For example, loops, hooks, or other securing mechanisms that attach to bone or tissue may be used in alternative embodiments of the present invention.

As one of ordinary skill in the relevant art would appreciate, embodiments of the drug-delivery sheath of the present invention need not be configured to have or to take on a shape that conforms with the surface of the implantable medical device with which it is implanted, as illustrated in FIGS. 2A, 2B, 3A and 3B. For example, in alternative embodiments, all or a portion of the drug-delivery sheath may be only partially conformable to the adjacent surface of the implantable medical device.

It should also be appreciated that the drug-delivery sheath of the present invention may be positioned in any position or orientation relative to the implantable medical device. In many applications, the drug-delivery sheath will be in direct contact with the implantable medical device. In other embodiments, the drug-delivery sheath will be in close proximity to the implantable medical device. Also, there are no restrictions regarding the side of the implantable medical device to which the drug-delivery sheath is adjacently positioned. Such a determination may be based on factors such as therapeutic benefits of the drugs, ease of implantation, long-term effects, desired migration or absorption path of the drugs, and other factors.

Figure 6:
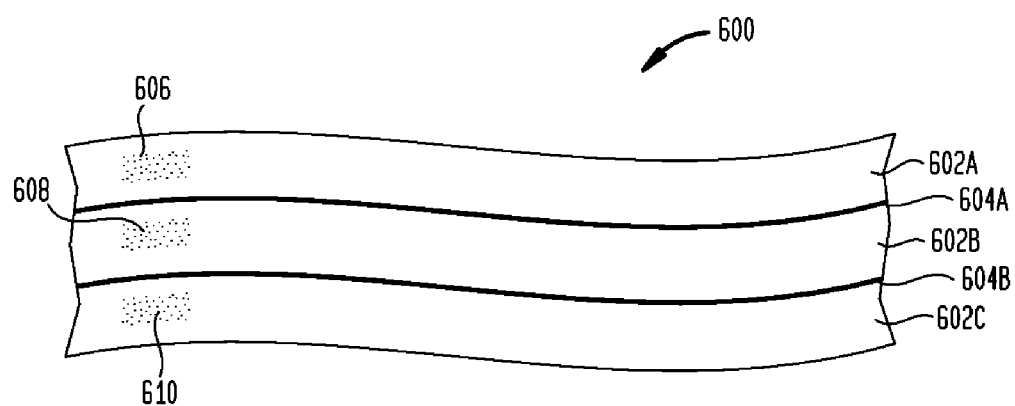
FIG. 6 is a side view of an alternative embodiment a drug-delivery sheath of the present invention.

It should also be appreciated that embodiments of the drug-delivery sheath of the present invention may be formed of one or more sheets or layers, as shown in FIG. 6. FIG. 6 is a side view of a portion of a drug-delivery sheath 600. Drug-delivery sheath 600 is a composite of three layers 602A-C joined by an adhesive 604A-B. Each layer 602 may serve a different function. For example, in the exemplary embodiment illustrated in FIG. 6, layer 602A carries a drug 606; layer 602B carries a drug 608; and layer 602C carries a drug. In an alternative embodiment, drugs 606, 608 and 610 are the same drug and/or are different drugs designed to treat the same or different conditions, and sheet(s) 602 and/or drug(s) 606, 608, 610 is/are configured such that the drug(s) is/are released at the same or different rate.

Furthermore, it is to be understood that one or more bioactive substances may be disposed on or in a portion or substantially all of each drug-delivery sheath depending on the particular application. For example, it may be beneficial for a drug-delivery sheath to have a bioactive substance disposed in only a portion of the sheath, with the remaining portion of the sheath configured as a carrier or supporting member for delivery of the bioactive substance to the recipient.

Embodiments of the drug-delivery sheath of the present invention may be constructed as a woven mesh. In such embodiments, the threads of the woven mesh may be treated with one or more drugs during the fabrication of the mesh, or the mesh may be treated with one or more drugs subsequent to fabrication and prior to implantation with the implantable medical device.

According to a further embodiment of the present invention, the drug-delivery sheath may be constructed of a polymeric material, in which molecules or other components of a bioactive substance disposed within the chemical structure of the drug-delivery sheath. One example of a polymeric material which may be used to construct an embodiment of a drug-delivery sheath of the present invention is silicone. Bioactive substances may be disposed within the silicone drug-delivery sheath such that the bioactive substance is released from the drug-delivery sheath.

According to another embodiment of the present invention, the surface of the drug-delivery sheath may be constructed to have microsurface geometry. Such a microsurface geometry may be constructed using nano-technologies, or may be constructed using other technologies presently known or developed in the future. Having a microsurface geometry may enable the drug-delivery sheath to be useful in partially or completely inhibiting growth of bacteria and other biological organisms on the surface of drug-delivery sheath.

It may be desirable for embodiments of the drug-delivery sheath of the present invention to be constructed of a resorbable material, so that while bioactive substances are being absorbed at the implant site, or after they are absorbed, the drug-delivery sheath may be partially or completely resorbed by the tissue surrounding the implant site. In certain embodiments, the drug-delivery sheath is comprised of a resorbable material that partially or completely degrades over time through interaction with various body fluids. In other embodiments, the drug-delivery sheath is comprised of a resorbable material that partially or completely degrades over time through exposure to body temperatures or fluids.

However, it may also be desirable for the drug-delivery sheath to be constructed of a non-resorbable material. The use of a non-resorbable material may offer different benefits from the use of a resorbable material, such as the continued provision of spacing or support for other tissue or implanted components. For example, the drug-delivery sheath may be made of a polymeric material configured to enable bioactive substances to be embedded within the structure of the polymeric material, and to release the bioactive substances either naturally or through the interaction of body fluids or body heat which may permeate the sheath. Furthermore, the drug-delivery sheath may have micro-surface geometry, such as those possible through advances in nano-technologies, which may limit or inhibit bacteria growth.

It is also to be understood that, although the embodiments of the drug-delivery sheath depicted herein have been constructed as a single continuous unit, in alternative embodiments the drug-delivery sheath may also be constructed from several parts joined together to form a single integrated sheath which is then capable of enveloping or surrounding at least a part of an implantable medical device. For example, in one alternative embodiment drug delivery sheath 300 (FIGS. 3A and 3B) comprises separate top and bottom sheaths 302A, 302B which are separately manufactured and joined together where necessary to form a pouch having desired dimensions for a particular implantable medical device.

In a further embodiment of the present invention, a bioactive substance to combat the formation of, or to remove, a biofilm. Such a bioactive substance may be an anti-bacterial drug that is embedded into the sheath of the present invention alone or in combination with other bioactive substances.

In another embodiment, the drug-delivery sheath is configured to be bonded to the surface of the implantable medical device thereby eliminating the space or gap that may form between the drug-delivery sheath and the adjacent surface of the medical device. The reduction and/or elimination of this gap reduces or eliminates the likelihood of bacterial growth between the two. In one embodiment, such bonding is performed in a sterile field immediately prior to surgery. Alternatively, such bonding is performed after the medical device is implanted in the patient. In another embodiment, such bonding is performed during manufacturing, such as one of the last few steps of manufacturing.

In one embodiment, the above bonding is performed by disposing a glue layer on the complementary component so that the drug-delivery sheath may be pressed on prior to surgery. This may be performed manually or with a simple press-tool that aligns the two components and presses them together with a predefined maximum pressure. Alternatively, a liquid glue may be applied between the medical device surface and the drug-delivery sheath. In one preferred embodiment, the liquid glue sets and/or cures rapidly. In another embodiment, a UV-cured glue is pre-applied to the component, or applied as a liquid, or is a separate component that is inserted between the drug-delivery sheath and the medical device. In one embodiment, a liquid perfluoropol polymer such as that described in International Application WO 2007/021620 A2 may be utilized. International Application WO 2007/021620 A2 is hereby incorporated by reference herein. Other adhesives which may be used include, bur are not limited to, fibrin glues, cyanoacrylates, polyurethane adhesives, silicone adhesives, and UC-cured acrylics. In another embodiment, chemical surface modification may be utilized to attain a desired bonding. For example, in one embodiment, covalently bonded proteins, or sulfonation may be performed to increase the wetability of the surface.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A kit of implantable components for implantation in a recipient, comprising:
   an implantable medical device;
   a drug delivery sheath physically separate from the device and configured to be implanted in the recipient proximate to the device, comprising: at least one pannicular substrate configured to be operably positioned adjacent to one or more surfaces of the device subsequent to the device's manufacture, and at least one drug carried on the at least one substrate so as to be released into the recipient, wherein the implantable medical device is an implantable component of a cochlear implant.

2. The kit of claim 1, wherein said at least one drug-delivery sheath is configured in the form of a pouch having interior dimensions that enable the pouch to receive and to partially or completely envelop the implantable medical device.

3. The kit of claim 1, wherein said at least one drug comprises one or more of the group consisting of: an anti-inflammatory drug; and an antibiotic.

4. The kit of claim 1, wherein the implantable component of the cochlear implant is a receiver/stimulator unit, and wherein the drug-delivery sheath is configured to be disposed between the recipient's skin and the receiver/stimulator unit when the receiver/stimulator unit is implanted in a recessed portion of the recipient's mastoid bone.

5. The kit of claim 1, wherein the drug-delivery sheath is configured as a pouch that at least partially envelops the implantable medical device.

6. The kit of claim 1, wherein said drug-delivery sheath comprises:
a top sheath; and
a bottom sheath.

7. The kit of claim 6, wherein said top and bottom sheaths are joined to each other to form a pouch dimensioned to receive the device.

8. The kit of claim 1, wherein the sheath is sufficiently flexible that the sheath may be manually urged to physically conform to a surface of the device.

9. The kit of claim 8, wherein the surface is on a side of the implantable medical device determined based on one or more factors such as therapeutic benefits of the drugs, ease of implantation, long-term effects, and desired migration path of the drug.

10. The kit of claim 1, wherein one or more exterior dimensions of the drug-delivery sheath approximate a corresponding exterior dimension of the implantable medical device.

11. The kit of claim 1, wherein the drug-delivery sheath further comprises:
one or more securing mechanisms each configured to attach the drug-delivery sheath to one of the implantable medical device, other implantable component or anatomical structure.

12. The kit if claim 11, wherein the one or more securing mechanisms are configured to be attached using one or more of sutures, staples and adhesives.

13. The kit of claim 11, wherein the securing mechanisms comprise one or more of the group consisting of: tabs; loops; and hooks.

14. The kit of claim 11, wherein the drug-delivery sheath comprises a substrate constructed of a polymeric material in which components of the drug are disposed within the chemical structure of the substrate.

15. The kit if claim 1, wherein said drug-delivery sheath is constructed of a resorbable material.

16. The kit if claim 1, wherein said drug-delivery sheath is formed of a plurality of pannicular substrates adhered together.

17. The kit of claim 16, wherein two or more of the substrates carry a different drug.

18. A complementary drug-delivery sheath for implantation into a recipient of an implantable medical device comprising:
a pannicular substrate having dimensions which enable the sheath to be implanted proximate to one or more surfaces of the device; and
at least one drug carried in the substrate for release into the body of the recipient,
wherein the implantable medical device is an implantable component of at least one of a cochlear implant, a fully implantable bone anchored hearing aid or a middle-ear implant.

19. The sheath of claim 18, wherein said drug-delivery sheath is configured in the form of a pouch having interior dimensions that enable the pouch to receive and to partially or completely envelop the implantable medical device.

20. The sheath of claim 18, wherein said at least one drug comprises one or more of the group consisting of: an anti-inflammatory drug; and an antibiotic.

21. The sheath of claim 18, wherein the implantable medical device is an implantable component of a cochlear implant.

22. The sheath of claim 21, wherein the implantable component of the cochlear implant is a receiver/stimulator unit, and wherein the drug-delivery sheath is configured to be disposed between the recipient's skin and the receiver/stimulator unit when the receiver/stimulator unit is implanted in a recessed portion of the recipient's mastoid bone.

23. The sheath of claim 18, wherein the drug-delivery sheath is configured as a pouch that at least partially envelops the implantable medical device.

24. The sheath of claim 18, wherein said drug-delivery sheath comprises:
a top sheath; and
a bottom sheath.

25. The sheath of claim 24, wherein said top and bottom sheaths are joined to each other to form a pouch dimensioned to receive the device.

26. The sheath of claim 18, wherein the sheath is sufficiently flexible that the sheath may be manually urged to physically conform to a surface of the device.

27. The sheath of claim 18, wherein one or more exterior dimensions of the drug-delivery sheath approximate a corresponding exterior dimension of the implantable medical device.

28. The sheath of claim 18, wherein the drug-delivery sheath further comprises:
one or more securing mechanisms each configured to attach the drug-delivery sheath to one of the implantable medical device, other implantable component or anatomical structure.

29. The sheath if claim 28, wherein the one or more securing mechanisms are configured to be attached using one or more of sutures, staples and adhesives.

30. The sheath of claim 28, wherein the securing mechanisms comprise one or more of the group consisting of: tabs; loops; and hooks.

31. The sheath if claim 18, wherein said drug-delivery sheath is formed of a plurality of pannicular substrates adhered together.

32. The sheath of claim 31, wherein two or more of the substrates carry a different drug.

33. The sheath of claim 18, wherein the drug-delivery sheath comprises a substrate constructed of a polymeric material in which components of the drug are disposed within the chemical structure of the substrate.

34. The sheath of claim 18, wherein said drug-delivery sheath is constructed of a resorbable material.

35. A kit of implantable components for implantation in a recipient, comprising:
an implantable medical device;
a drug delivery sheath physically separate from the device and configured to be implanted in the recipient proximate to the device, comprising: at least one pannicular substrate configured to be operably positioned adjacent to one or more surfaces of the device subsequent to the device's manufacture, and at least one drug carried on the at least one substrate so as to be released into the recipient,
wherein the implantable medical device is an implantable component of at least one of a cochlear implant, a fully implantable bone anchored hearing aid or a middle-ear implant.

* * * * *